United States Patent [19]
Hanazato et al.

[11] Patent Number: 5,543,024
[45] Date of Patent: Aug. 6, 1996

[54] GLUCOSE SENSITIVE FET SENSOR AND METHOD OF MAKING SAME

[75] Inventors: Yoshio Hanazato; Mamiko Nakako; Satoru Shiono; Kenichi Inatomi, all of Amagasaki, Japan

[73] Assignee: Mitsubishi Denki Kabushiki Kaisha, Tokyo, Japan

[21] Appl. No.: 587,660

[22] Filed: Sep. 25, 1990

Related U.S. Application Data

[63] Continuation of Ser. No. 162,590, Mar. 1, 1988, abandoned.

[30] Foreign Application Priority Data

Mar. 3, 1987 [JP] Japan ................... 62-46660
Sep. 10, 1987 [JP] Japan ................... 62-225342

[51] Int. Cl.⁶ ............................................. G01N 27/327
[52] U.S. Cl. .......................... 204/403; 204/418; 427/58; 427/385.5; 427/430.1; 427/443.2; 435/14; 435/817; 436/531; 436/806
[58] Field of Search ........................ 204/153.12, 403, 204/418; 435/14, 817; 436/806, 531; 427/58, 385.5, 430.1, 443.2

[56] References Cited

U.S. PATENT DOCUMENTS

| | | | |
|---|---|---|---|
| 3,979,274 | 9/1976 | Newman | 204/403 |
| 4,340,448 | 7/1982 | Schiller et al. | 204/403 |
| 4,353,983 | 10/1982 | Siddqi | 204/403 |
| 4,375,399 | 3/1983 | Havas et al. | 204/403 |
| 4,404,066 | 9/1983 | Johnson | 204/403 |
| 4,484,987 | 11/1984 | Gough | 204/403 |
| 4,547,280 | 10/1985 | Karasawa et al. | 204/403 |
| 4,552,840 | 11/1985 | Riffer | 204/403 |
| 4,721,677 | 1/1988 | Clark | 204/403 |
| 4,894,339 | 1/1990 | Hanazato et al. | 204/403 |

OTHER PUBLICATIONS

"Enzyme Nomenclature", 1978 Month unavailable, Academic Press, pp. 236 and 237.
Hanazato et al, "Proceedings of the International Meeting on Chemical Sensors", pp. 513–518, 1983 Month unavailable.
Pocker et al, "Hydrolysis of D–Glucono–δ–lactone. I. General Acid–Base Catalysis, Solvent Deuterium Isotope Effects, and Transition State Characterization", J. Amer. Chem. Soc. 95, pp. 113–119 (1973) Month unavailable.

*Primary Examiner*—T. Tung
*Attorney, Agent, or Firm*—Leydig, Voit & Mayer

[57] ABSTRACT

A glucose sensitive FET sensor is provided which includes a substrate, a source electrode formed in the substrate, a drain electrode formed in the substrate, a hydrogen ion sensitive film formed on the substrate to cover the source electrode and the drain electrode, and a thin enzyme immobilized membrane formed on the hydrogen ion sensitive film and containing glucose oxidase and gluconolactonase. Also provided is a method of producing a glucose sensitive FET sensor which includes the steps of preparing an enzyme immobilized membrane as a thin film containing glucose oxidase and gluconolactonase and forming the membrane on a hydrogen ion sensitive film which is formed on a substrate to cover a source electrode and a drain electrode, both of which are formed in the substrate.

11 Claims, 5 Drawing Sheets

GLUCOSE SENSITIVE FET SENSOR AND METHOD OF MAKING SAME

This application is a continuation of application Ser. No. 07/162,590, filed Mar. 1, 1988, now abandoned.

BACKGROUND OF THE INVENTION

The present invention relates to a glucose sensitive FET (field-effect transistor) sensor having a high degree of sensitivity and a high-speed response, and to a method of making the same.

DESCRIPTION OF THE PRIOR ART

It is well known that measurement of the concentrations of various organic substances in body fluids such as blood or urine is extremely important in clinical diagnoses. For this reason, efforts have thus far been directed to development of various quantitative measurement methods and improvements therein. In the field of clinical diagnoses in particular, there has been a demand for the development of a quantitative measurement method which employs a sensor of small size with high-speed response since it is necessary to handle trace amounts of samples or to conduct very rapid measurement. To meet such demands, an enzyme FET sensor has been developed which is constituted by a combination of an enzyme immobilized membrane and an ion sensitive FET (ISFET) which is an ion sensor that can be micro finished by known semiconductor production techniques.

FIG. 1 is a diagrammatic cross-sectional view illustrating a prior art glucose sensitive FET sensor. In FIG. 1, an ISFET element 1 includes a substrate 2, a source electrode 3 and a drain electrode 4 both of which are formed in the substrate 2, and a hydrogen ion sensitive film 5 formed on the surface of the substrate 2 such as to cover the source electrode 3 and the drain electrode 4. The hydrogen ion sensitive film 5 is a silicon nitride film which also serves as an electrically insulating film. An ion sensitive portion 5a is formed at the portion of the surface of the hydrogen ion sensitive film 5 which is defined between the source electrode 3 and the drain electrode 4. An enzyme immobilized membrane 7 including glucose oxidase 6 is formed on the sensitive portion 5a. The enzyme immobilized membrane 7 and the ISFET element 1 constitute in combination a glucose sensitive FET sensor 8. Also, a reference electrode 9 is located in the vicinity of the enzyme immobilized membrane 7 so as to apply a gate voltage between a semiconductor portion of the sensor 8 and an aqueous solution through the intermediary aqueous solution.

The prior art glucose sensitive FET sensor 8 is constructed in the above-described manner, and the ISFET element 1 is adapted to respond to hydrogen ions in the aqueous solution to exhibit a response of about 50 mV/pH in a pH range of 1–10. As stated in, for example, "Sensors and Actuators", published in 1985, vol. 7, page 233, glucose oxidase is an enzyme which selectively oxidizes β-D-glucose, and acts to decompose β-D-glucose into D-glucono-δ-lactone under the conditions of coexistence with oxygen, as represented by the following formula. The thus-generated D-glucono-δ-lactone is changed into gluconic acid in the aqueous solution by a spontaneous hydrolytic reaction.

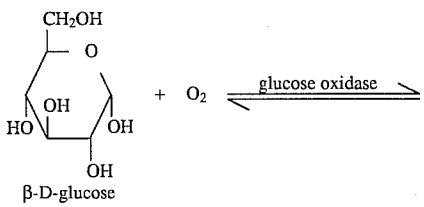

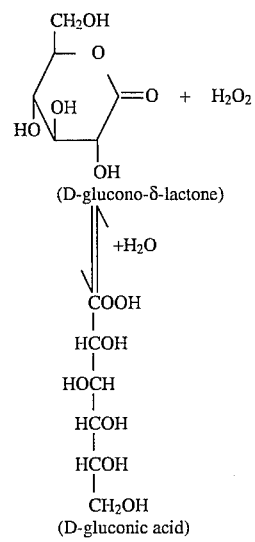

If β-D-glucose is present in an aqueous solution to be measured, the enzyme reaction shown in the above formula occurs in the enzyme immobilized membrane 7 which contains the glucose oxidase 6 and thus gluconic acid is generated. Therefore, the pH value in the enzyme immobilized membrane 7 becomes small. The ISFET element 1 which underlies the enzyme immobilized membrane 7 detects this pH variation, thereby responding to the glucose concentration.

Since the above-described glucose sensitive FET sensor 8 employs glucose oxidase as an enzyme, the hydrolysis of the D-glucono-δ-lactone into D-gluconic acid is a rate-determining step in the reaction presented by the above reaction equations. Therefore, the sensitivity and response speed of the glucose sensitive FET sensor 8 are restrained by the slow speed of the hydrolytic reaction. This leads to the problem that it is impossible to further enhance the sensitivity and response speed of the glucose sensitive FET sensor 8.

SUMMARY OF THE INVENTION

It is, therefore, an object of the present invention to provide an inexpensive glucose sensitive FET sensor capable of responding with high sensitivity and at high speed, as well as a method of making the same.

To achieve the above and other objects, in accordance with the present invention, there is provided a glucose sensitive FET sensor comprising: a substrate; a source electrode formed in the substrate; a drain electrode formed in the substrate; a hydrogen ion sensitive film formed on the substrate to cover the source electrode and the drain electrode; and an enzyme immobilized membrane formed on the hydrogen ion sensitive film and containing glucose oxidase and gluconolactonase.

In accordance with the present invention, gluconolactonase contained in the enzyme immobilized membrane accelerates the hydrolytic reaction of D-glucono-δ-lactone by its enzyme reaction, in which the hydrolysis is a rate-determining step of the previously-noted formula. Therefore, D-gluconic acid is rapidly generated from β-D-glucose in the enzyme immobilized membrane. More specifically, since the amount of gluconic acid accumulated in the enzyme immobilized membrane increases, the sensitivity of the glucose sensitive FET sensor is improved. In addition, since the rate of acid generation increases, the response of the sensor is accelerated.

Furthermore, in accordance with the present invention, since a water soluble photosensitive resin can be employed to form a very thin enzyme immobilized membrane, it is possible to obtain a sensor exhibiting high sensitivity with high-speed response.

BRIEF DESCRIPTION OF THE DRAWINGS

The present invention will be more readily apparent from the following detailed description of a few preferred embodiments thereof when taken in conjunction with the accompanying drawings, in which.

DESCRIPTION OF THE PREFERRED EMBODIMENTS

Figure 1:
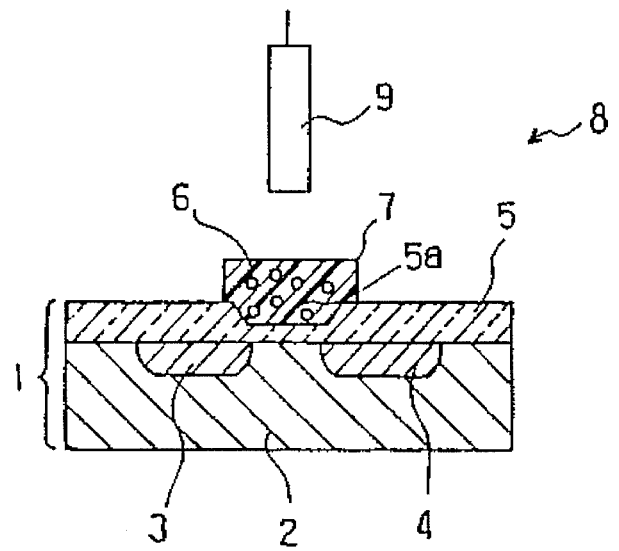
FIG. 1 is a diagrammatic cross section illustrating a prior art glucose sensitive FET sensor.
Figure 2:
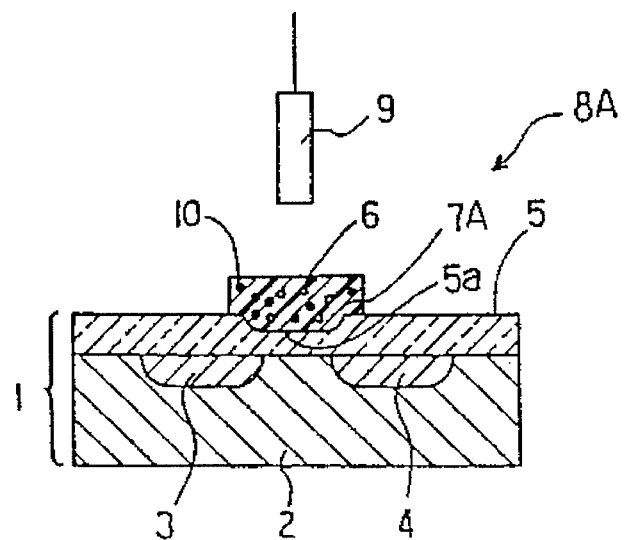
FIG. 2 is a diagrammatic cross section illustrating a glucose sensitive FET sensor in accordance with the present invention.

FIG. 2 is a diagrammatic cross section illustrating one preferred embodiment of the present invention. In FIG. 2, the respective portions 1 to 6 and 9 are identical to the corresponding portions incorporated in the prior art glucose sensitive FET sensor 8 as shown in FIG. 1, and therefore act in the same manner as described above. An enzyme immobilized membrane 7A which contains a glucose oxidase 6 and gluconolactonase 10 is formed on the ion sensitive portion 5a of a hydrogen ion sensitive film 5 of an ISFET element 1. The enzyme immobilized membrane 7A and the ISFET element 1 constitute in combination a glucose sensitive FET sensor 8A.

The glucose sensitive FET sensor 8A having the above-described structure was produced in the following manner. An aqueous solution of a water soluble photosensitive resin was prepared by dissolving a 2, 5-bis(4'-azide-2'-sulfobenzal) cyclopentanone sodium salt (produced by Tokyo Ohka-kogyo Co., Ltd.) in, for example, an aqueous solution containing a 20 weight percent water soluble resin of polyvinyl pyrrolidone having a molecular weight of about 360,000, at about 10 percent by weight of polyvinyl pyrrolidone.

Glucose oxidase having an activity of 110 U/mg was dissolved in an aqueous solution, and the aqueous solution of glucose oxidase was concentrated to prepare a concentrated glucose oxidase solution. The activity of this concentrated glucose oxidase solution was about 12,000 U/ml at pH 7.0.

Gluconolactonase, which was separated from *Aspergillus niger* and purified, was dissolved in an aqueous solution. The aqueous solution containing the gluconolactonase was concentrated to prepare a concentrated gluconolactonase solution. The activity of this concentrated gluconolactonase solution was about 60,000 U/ml at pH 7.0.

An amount of 15 μl of a suitably diluted portion of the concentrated gluconolactonase solution was added to 15 μl of concentrated glucose oxidase solution which was prepared in the above-described manner. The mixed solution obtained was mixed with 30 μl of the aqueous solution of the water soluble photosensitive resin which was prepared in the above-described manner. Thus, the mixed solution of enzyme-water soluble photosensitive resin was obtained. The mixed solution obtained was coated on the hydrogen ion sensitive film 5 of the ISFET element 1. Then, a uniform film was formed on an ISFET by the coating method using a spinner, followed by drying. Subsequently, the mixed solution of the enzyme-water soluble photosensitive resin was exposed to light irradiation for three seconds through a photomask by means of a 250 W super high voltage mercury-arc lamp, followed by developing in distilled water, thereby forming the patterned enzyme immobilized membrane 7A, and thus preparing the glucose sensitive FET sensor 8A.

Subsequently, 10 mM of a PIPES-NaOH buffer solution (pH 7.0) was employed to measure the performance of the glucose sensitive FET sensor 8A obtained at 30° C.

Figure 3:
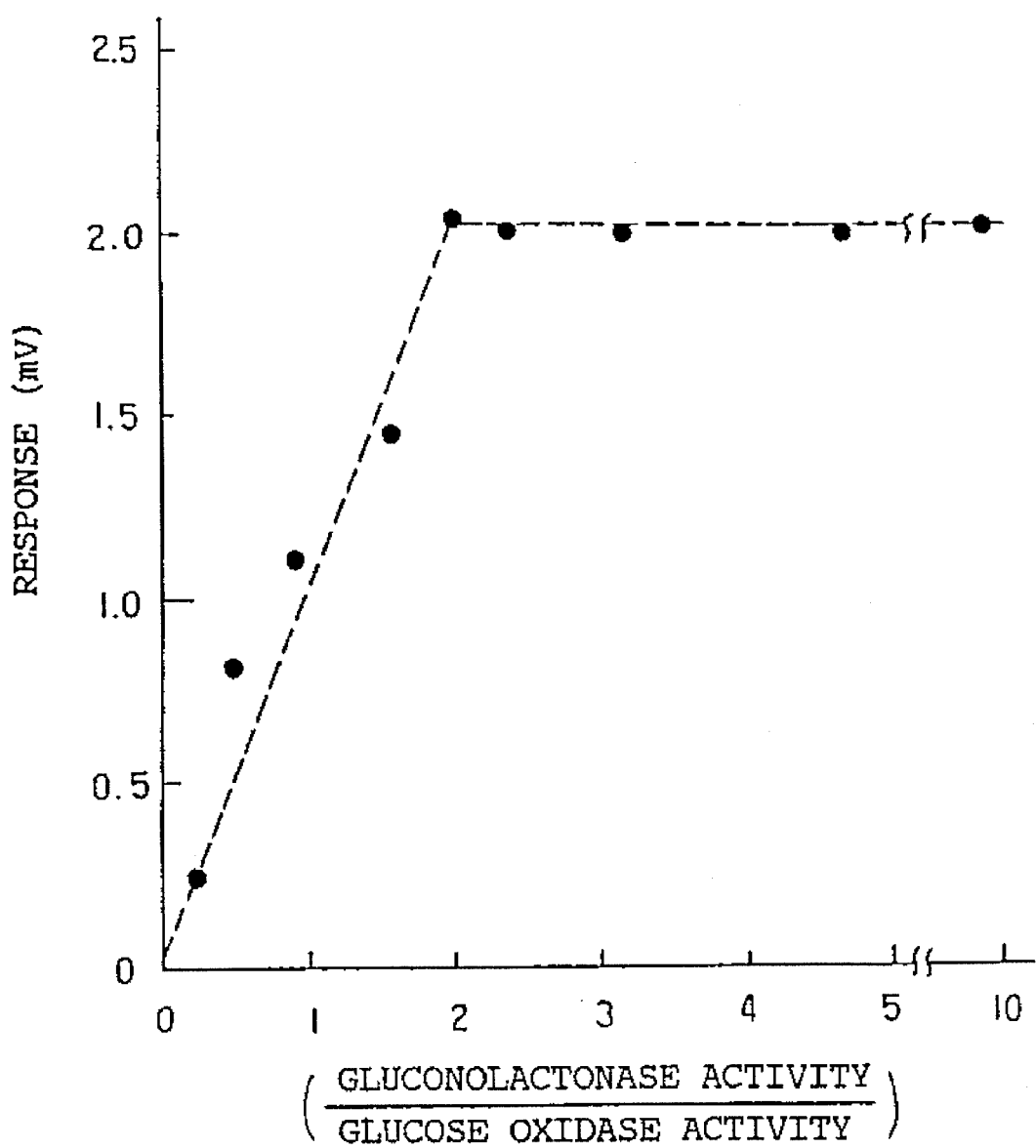
FIG. 3 is a graph showing responses corresponding to the activity of gluconolactonase to glucose oxidase.

FIG. 3 is a graph showing the magnitude (mV) of response of the glucose sensitive FET sensor 8A when the activity of gluconolactonase was varied while the activity of glucose oxidase was made constant. This magnitude of response of the sensor 8A represents the result of measurement when the glucose concentration is 0.5 mM. As can be seen from FIG. 3, when the activity ratio of glucose oxidase to gluconolactonase is less than 1:2, as the activity of glucose lactonase increases, the magnitude of response increases. When that activity ratio is equal to or greater than 1:2, the magnitude of response is saturated. Therefore, it is understood that the aforesaid activity ratio needs to be at least 1:0.5 in order to obtain a sensor 8A with sufficiently high sensitivity; particularly, when the activity ratio is in the range of up to 1:10, high sensitivity can be achieved. In addition, when account is taken of the high costs involved in obtaining enzyme samples, it is advantageous to use the smallest possible amount of enzyme. Accordingly, a particularly desirable composition ratio ranges in activity ratios of from 1:2 to 1:3.

Figure 4:
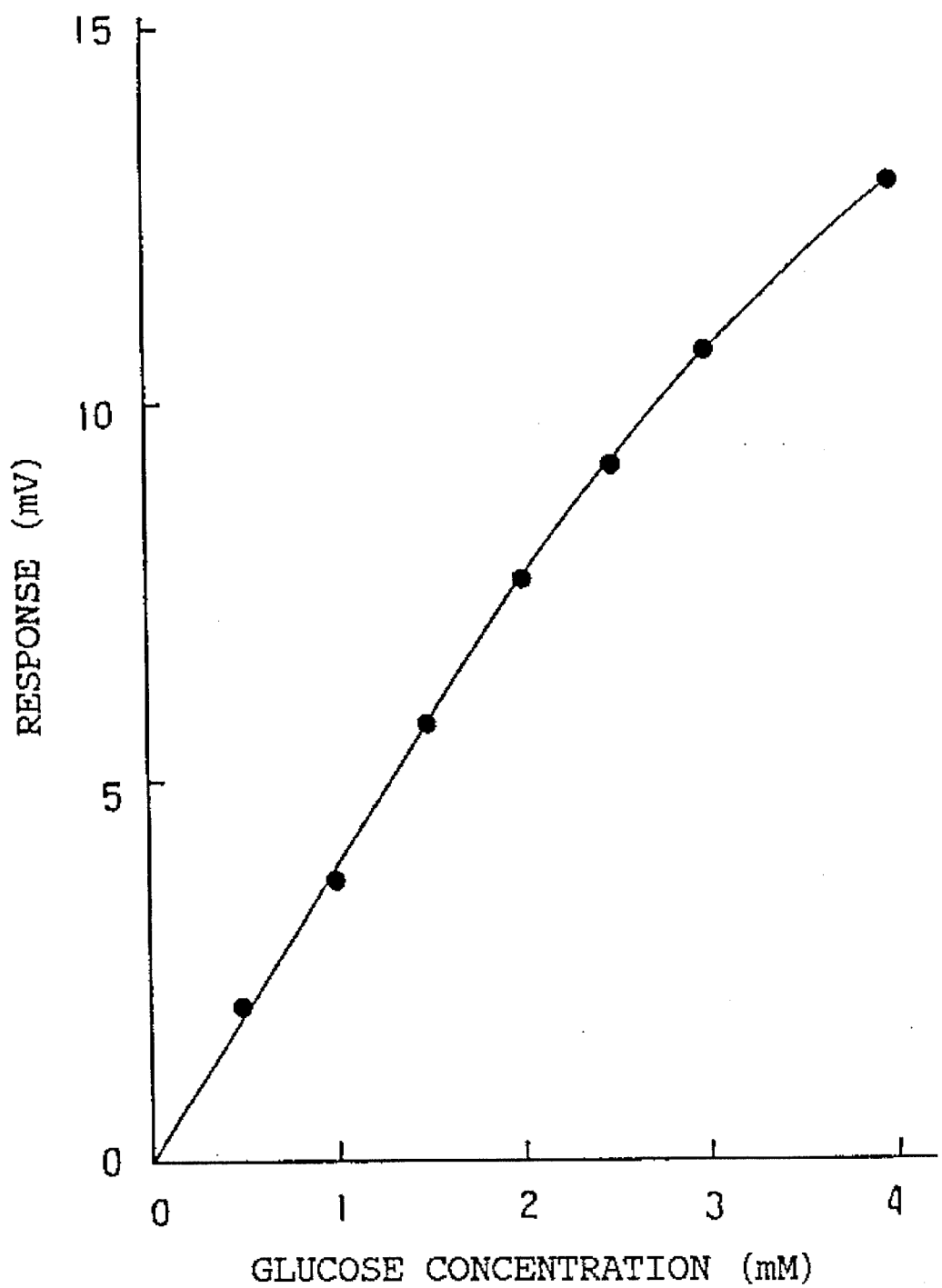
FIG. 4 is a calibration curve of the glucose sensitive FET sensor in accordance with the present invention.

FIG. 4 is a calibration curve of the glucose sensitivity FET sensor 8A which was produced under the condition that the activity ratio of glucose oxidase to gluconolactonase was 1:2. It is understood from FIG. 4 that the sensor 8A exhibited a linear response up to the glucose concentration 2 mM. In addition, the sensor 8A exhibited an extremely high speed response, i.e., five seconds. These advantages result from the fact that the film thickness of the enzyme immobilized membrane 7A produced from the water soluble photosensitive resin can be formed into an extremely thin film of about 1 μm.

Figure 5:
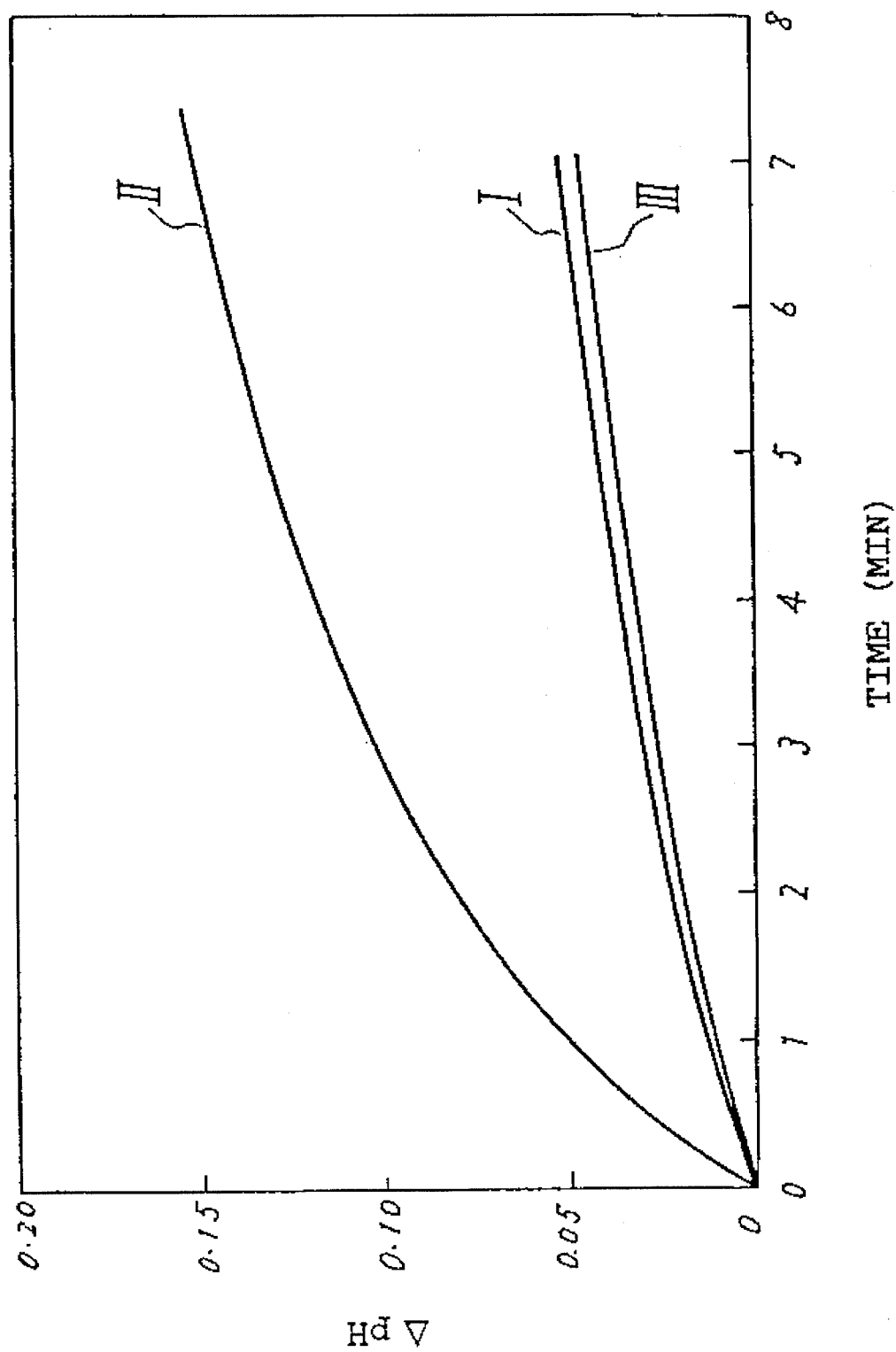
FIG. 5 is a characteristic chart showing the hydrolysis of D-glucono-δ-lactone in accordance with the present invention employing glucose oxidase containing gluconolactonase.

FIG. 5 is a characteristic chart of the hydrolytic reactions of D-glucono-δ-lactone, which were each monitored by a pH electrode. Samples used were glucose oxidase (I) (glucose oxidase activity: 133 U/mg) which was a highly purified preparation from *Aspergillus niger* and glucose oxidase (II) (glucose oxidase activity: 29.3 U/mg), a crude preparation containing gluconolactonase from *Aspergillus niger*. In FIG. 5, the vertical axis represents variations in pH (Δ pH) and the horizontal axis represents time (min). Curve I represents the results of the hydrolytic reaction of glucose oxidase (I), curve II glucose oxidase (II) containing gluconolactonase, and curve III the spontaneous hydrolytic reaction of D-glucono-δ-lactone without glucose oxidase (I) or (II). Measurement was made employing 10 mM of a PIPES-NaOH buffer solution (pH 6.94) at 35° C. It is found from FIG. 5 that curve I substantially coincides with curve III. In contrast, it is understood from curve II that D-glucono-δ-lactone is hydrolyzed rapidly to gluconic acid when glucose oxidase (II) containing gluconolactonase is employed.

An aqueous solution of a water soluble photosensitive resin was prepared by dissolving a 2, 5-bis(4'-azide-2'-sulfobenzal) cyclopentanone sodium salt (produced by Tokyo Ohkakogyo Co., Ltd.) in, for example, an aqueous solution containing a 10 weight percent water soluble resin solution of polyvinyl pyrrolidone having a molecular weight of about 360,000, at about 10 percent by weight of polyvinyl pyrrolidone. 2 mg of a mixture of glucose oxidase (I) and glucose oxidase (II) containing gluconolactonase and 10 mg of bovine serum albumin were dissolved in 0.2 ml of the above-described aqueous solution, to prepare a uniform solution. The thus-prepared mixed aqueous solution of the enzyme-water soluble photosensitive resin was coated on the hydrogen ion sensitive film 5 which serves as the channel portion of a pH-ISFET element 1 that included a source electrode 3 and a drain electrode 4. Then, a uniform film was formed on an ISFET by the coating method using a spinner, followed by drying. Subsequently, the mixed solution of the enzyme-water soluble photosensitive resin was exposed to light irradiation for five seconds through a photomask by means of a 250 W super high voltage mercury-arc lamp, followed by developing in a 3% glutaraldehyde aqueous solution. In this manner, the patterned enzyme immobilized membrane of glucose oxidase was formed, and thus the glucose sensitive FET sensors were prepared to serve as examples of the present invention.

Figure 6:
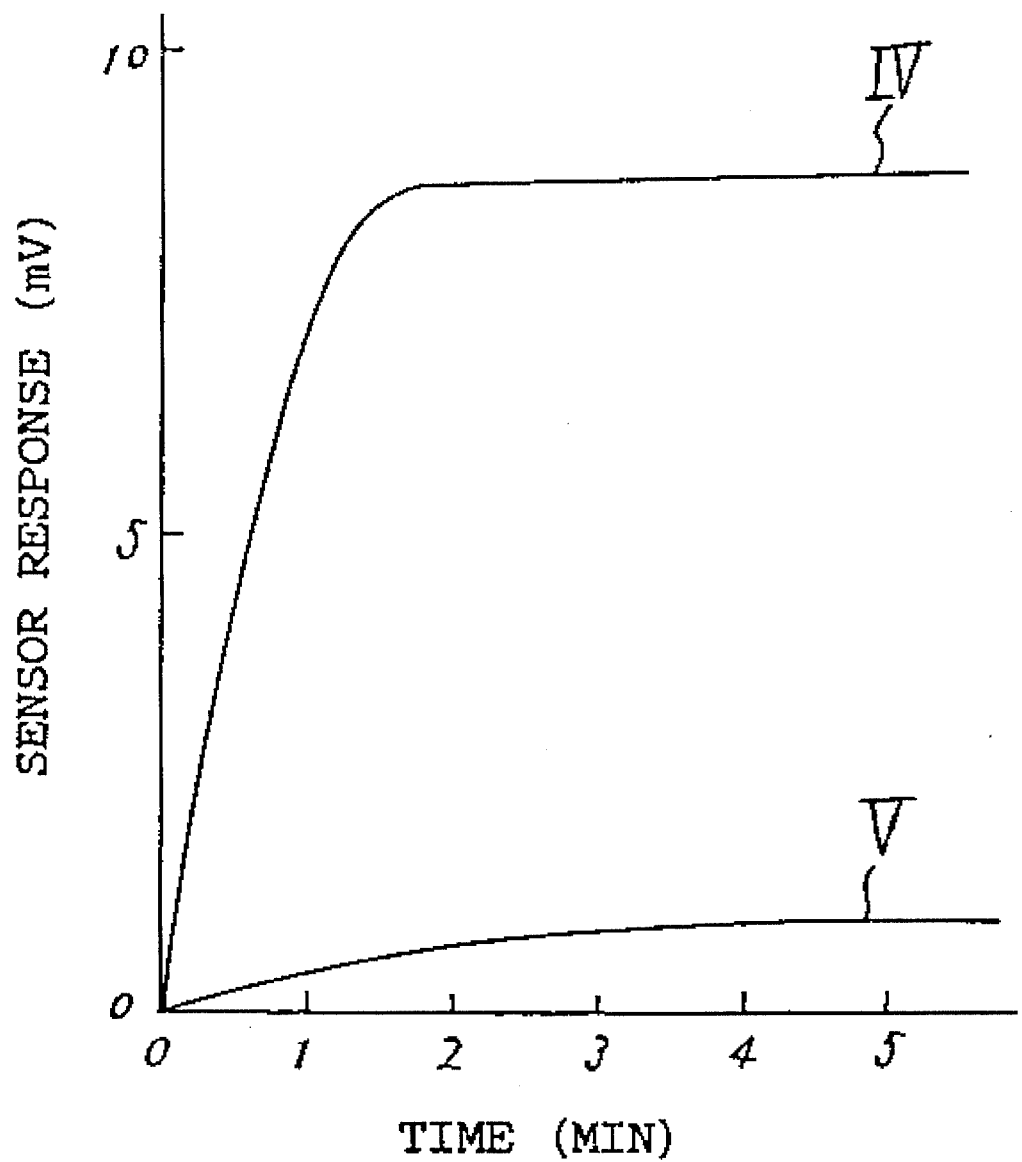
FIG. 6 is a chart comparatively showing the response characteristics of the glucose sensitive FET sensors of the present invention and the prior art.

By the above-described method, five examples of glucose sensitive FET sensors of the present invention were produced by employing glucose oxidase (I) and glucose oxidase (II) containing gluconolactonase at the mixed ratios (weight ratios) as shown in the following table. Also, for the purpose of comparison, glucose oxidase (I) alone was employed to prepare a glucose sensitive FET sensor as a comparative example using the aforesaid method. The table further shows the magnitude of response (mV) of each of these sensors with respect to 40 mg/dl of D-glucose. Measurement was made employing 10 mM of a PIPES-NaOH buffer solution (pH 7.08) at 25° C. FIG. 6 is a chart comparatively showing the response characteristics of the glucose sensitive FET sensor in accordance with the present invention and the prior art glucose sensitive FET sensor. In FIG. 6, the vertical axis represents the magnitude of response (mV) of the sensors and the horizontal axis represents time (min). Curve IV represents the response curve of Example 1 of the present invention, and curve V the response curve of the Comparative Example.

TABLE

|  | Example 1 | Example 2 | Example 3 | Example 4 | Example 5 | Comparative Example |
|---|---|---|---|---|---|---|
| Mixture of (II):(I) | 5:0 | 4:1 | 3:2 | 2:3 | 1:4 | 0:5 |
| Response to 40 mg/dl glucose (mV) | 8.65 | 11.42 | 14.80 | 12.52 | 8.17 | 0.93 |

As can be seen from the above Table and FIG. 6, the examples employing glucose oxidase (II) containing gluconolactonase excel in both sensitivity and response speed as compared with the comparative example employing glucose oxidase (I) alone. It is to be noted that the highest level of sensitivity was achieved by the glucose sensitive FET sensor having an enzyme immobilized membrane composed of the 3:2 mixture of glucose oxidase (I) and glucose oxidase (II) containing gluconolactonase.

For the purpose of illustration, gluconolactonase separated from *Aspergillus niger* was employed in the above-described examples. However, the enzymes contained in yeast, *Preudomonas fluorescens, Sacchoronyces cerevisias, Escherichia coli,* porcine liver, beef liver or the like may be purified and used as gluconolactonase. In this case as well, it is possible to achieve an effect similar to the one described above.

In the previously-described examples, an optical cross linking method was illustratively used as an enzyme immobilizing method. However, it is of course possible to utilize any enzyme immobilizing method that enables both stable immobilization of an enzyme and formation of a thin film.

In the above-described examples, glucose oxidase and gluconolactonase were mixed together to prepare an enzyme solution. However, there are some instances where gluconolactonase is present as an impurity in glucose oxidase, and such glucose oxidase may be employed directly. In this case, if the activity ratio at pH 7 of glucose oxidase to gluconolactonase is in the range of 1:0.5 to 1:10, such an enzyme can be directly used to produce a proper effect, similar to the examples described above.

While a few presently preferred embodiments of the present invention have been shown and described herein, it will be apparent to those skilled in the art that various changes and/or modifications thereof can be made without departing from the spirit and scope of the invention as defined in the appended claims.

What is claimed is:

1. A glucose sensitive FET sensor, comprising:

a substrate;

a source electrode formed in said substrate;

a drain electrode formed in said substrate;

a hydrogen ion sensitive film formed on said substrate to cover said source electrode and said drain electrode; and a thin enzyme immobilized membrane formed on said hydrogen ion sensitive film and containing glucose oxidase and gluconolactonase.

2. A glucose sensitive FET sensor as claimed in claim 1, wherein the activity ratio of said glucose oxidase to said gluconolactonase is in the range of from 1:0.5 to 1:10.

3. A glucose sensitive FET sensor as claimed in claim 1, wherein the activity ratio of said glucose oxidase to said gluconolactonase is in the range of from 1:2 to 1:3.

4. A glucose sensitive FET sensor as claimed in claim 1 wherein the thickness of said thin enzyme immobilized membrane is about 1 μm.

5. A glucose sensitive FET sensor as claimed in claim 1 wherein said film enzyme immobilized membrane is formed from 2,5-bis (4'-azide-2'-sulfobenzal) cyclopentanone sodium salt and a water soluble resin of polyvinyl pyrrolidone in addition to said glucose oxidase and gluconolactonase.

6. A glucose sensitive FET sensor as claimed in claim 5 wherein said polyvinyl pyrrolidone has a molecular weight of 360,000.

7. A method of producing a glucose sensitive FET sensor, comprising the steps of:

preparing an enzyme immobilized membrane as a thin film containing glucose oxidase and gluconolactonase; and forming said membrane on a hydrogen ion sensitive film which is formed on a substrate to cover a source electrode and a drain electrode both of which are formed in said substrate.

8. A method of producing a glucose sensitive FET sensor as claimed in claim 7, wherein said preparation step of said membrane further comprises the steps of:

preparing an aqueous solution of a water soluble photosensitive resin which contains glucose oxidase and gluconolactonase;

coating said aqueous solution of said water soluble photosensitive resin on said hydrogen ion sensitive film formed on said substrate to cover said source electrode and said drain electrode thereon; and irradiating a predetermined portion of said aqueous solution coated on said substrate with light, thereby forming an enzyme immobilized membrane as a thin film.

9. A method of producing a glucose sensitive FET sensor as claimed in claim 7, wherein the activity ratio of said glucose oxidase to said gluconolactonase is in the range of from 1:0.5 to 1:10.

10. A method of producing a glucose sensitive FET sensor as claimed in claim 7, wherein the activity ratio of said glucose oxidase to said gluconolactonase is in the range of from 1:2 to 1:3.

11. A method of producing a glucose sensitive FET sensor as claimed in claim 7, wherein the thickness of said enzyme immobilized membrane is in the micron order.

\* \* \* \* \*